US00PP32021P2

(12) United States Plant Patent
LaBonte et al.

(10) Patent No.: US PP32,021 P2
(45) Date of Patent: Jul. 28, 2020

(54) SWEETPOTATO PLANT NAMED 'LA13-81'

(50) Latin Name: ***Ipomoea batatas* (L.) Lam.**
Varietal Denomination: LA13-81

(71) Applicant: The Board of Supervisors of Louisiana State University and Agricultural and Mechanical College, Baton Rouge, LA (US)

(72) Inventors: Don R. LaBonte, Baton Rouge, LA (US); Arthur Q. Villordon, Chase, LA (US); Tara P. Smith, Alexandria, LA (US); Christopher A. Clark, Baton Rouge, LA (US)

(73) Assignee: THE BOARD OF SUPERVISORS OF LOUISIANA STATE UNIVERSITY AND AGRICULTURAL AND MECHANICAL COLLEGE, Baton Rouge, LA (US)

( * ) Notice: Subject to any disclaimer, the term of this patent is extended or adjusted under 35 U.S.C. 154(b) by 0 days.

(21) Appl. No.: 16/350,993

(22) Filed: Feb. 8, 2019

(51) Int. Cl.
*A01H 5/06* (2018.01)
*A01H 6/00* (2018.01)

(52) U.S. Cl.
USPC ..... Plt./258

(58) Field of Classification Search
USPC ..... Plt./258, 263.1, 226, 256
CPC ... A01H 5/06; A01H 5/02; A01H 5/12; A01H 5/00; A01H 5/04; A01H 6/00
See application file for complete search history.

(56) References Cited

U.S. PATENT DOCUMENTS

PP23,785 P3 * 7/2013 LaBonte ..... A01H 5/06 Plt./258

OTHER PUBLICATIONS

Osborne et al. New sweet potato variety on the way for Louisiana growers. 2018 LSU Ag Center, retrieved on Oct. 30, 2019, retrieved from the Internet at https://www.lsuagcenter.com/profiles/rbogren/articles/page1534945274695, 8 pp. (Year: 2018).*

* cited by examiner

*Primary Examiner* — June Hwu
(74) *Attorney, Agent, or Firm* — Baker Donelson

(57) ABSTRACT

A new variety of sweetpotato, identified as 'LA13-81', is disclosed having disease resistance to both *Fusarium* wilt and *Streptomyces* soil rot; an orange flesh storage root and deep red-purple skin, and high yield characteristics.

3 Drawing Sheets

Genus and species name: *Ipomoea batatas* (L.) Lam.
Variety denomination: 'LA13-81'.

BACKGROUND OF THE INVENTION

Sweetpotatoes, unlike Irish potatoes (*Solanum tuberosum*), are not tuber propagated plants. A "tuber" is a short, thickened portion of an underground branch. Along a tuber "eyes" are found, each of which comprises a ridge bearing a scale-like leaf (analogous to a branch leaf) having minute meristematic buds in the axial of the leaf. By contrast, sweetpotato roots are developmentally and anatomically true roots, lacking meristematic buds, and are not derived from an underground branch. Sweetpotatoes do not form tubers.

SUMMARY OF THE INVENTION

This invention pertains to a new and distinct variety of sweetpotato. This new and distinct sweetpotato variety demonstrates superior disease resistance to *Fusarium* wilt and exhibits a storage root with orange flesh. It also demonstrates a deep red-purple skin in comparison to '05-111' with a light to medium rose skin.

This new and distinct sweetpotato variety is identified as 'LA13-81' and is characterized by a storage root with orange flesh, consistent shape, and a deep red-purple skin.

DETAILED BOTANICAL DESCRIPTION

This new variety of sweetpotato, named 'LA13-81', resulted from an open-pollinated cross performed in 2012 to the patented female parent 'Bonita' (U.S. Plant Pat. No. 22,719 P3). The male parent was unknown. Five patented male parents ('05-111' patented U.S. Plant Pat. No. 23,761 P3; 'Evangeline' patented U.S. Plant Pat. No. 19,710 P3; 'LA06-52' patented U.S. Plant Pat. No. 26,735 P3; '07-146' U.S. Plant Pat. No. 23,785 P3; 'LA04-175' U.S. Plant Pat. No. 25,308 P3) were among the potential pollen sources in the crossing nursery. 'LA13-81' was developed to provide a variety with characteristics similar to '05-111', but with a red-purple skin. The female parent 'Bonita' has white fleshed storage roots.

Plants of 'LA13-81' and variety '05-111' can be differentiated. Abaxial and axial veins of 'LA13-81' are red purple

[5 R (red) P (purple) (2/6)]. '05-111' has no red hue to veins. Roots of 'LA13-81' are a deep red-purple skin and can be differentiated from the light tan of the female parent 'Bonita' (U.S. Plant Pat. No. 22,719 P3). Color terminology used herein is in accordance with the MUNSELL® Book of Color (2003 Edition, Munsell Color, GretagMacbeth LLC, 617 Little Britain Road, New Windsor, N.Y. 12553-6148). The color descriptions and color illustrations are as nearly true as is reasonably possible. However, it is understood that both color and other phenotypic expressions described herein may vary from plant to plant with differences in growth, environment and cultural conditions, without any change in the genotype of the variety 'LA13-81'.

'LA13-81' roots were stored during the winter in Chase, La. 'LA13-81' was planted the following spring, resulting in approximately 8-10 sprouts per root. Cuttings from the sprouts were transplanted successfully for asexual reproduction in Chase, La. Asexual propagation of the new cultivar by cuttings has shown that the unique features of this new sweetpotato were stable and that the plant reproduced true to type in successive generations of asexual propagation. Plants described herein were 90 days in age from planting in full sun field plantings.

Figure 1:
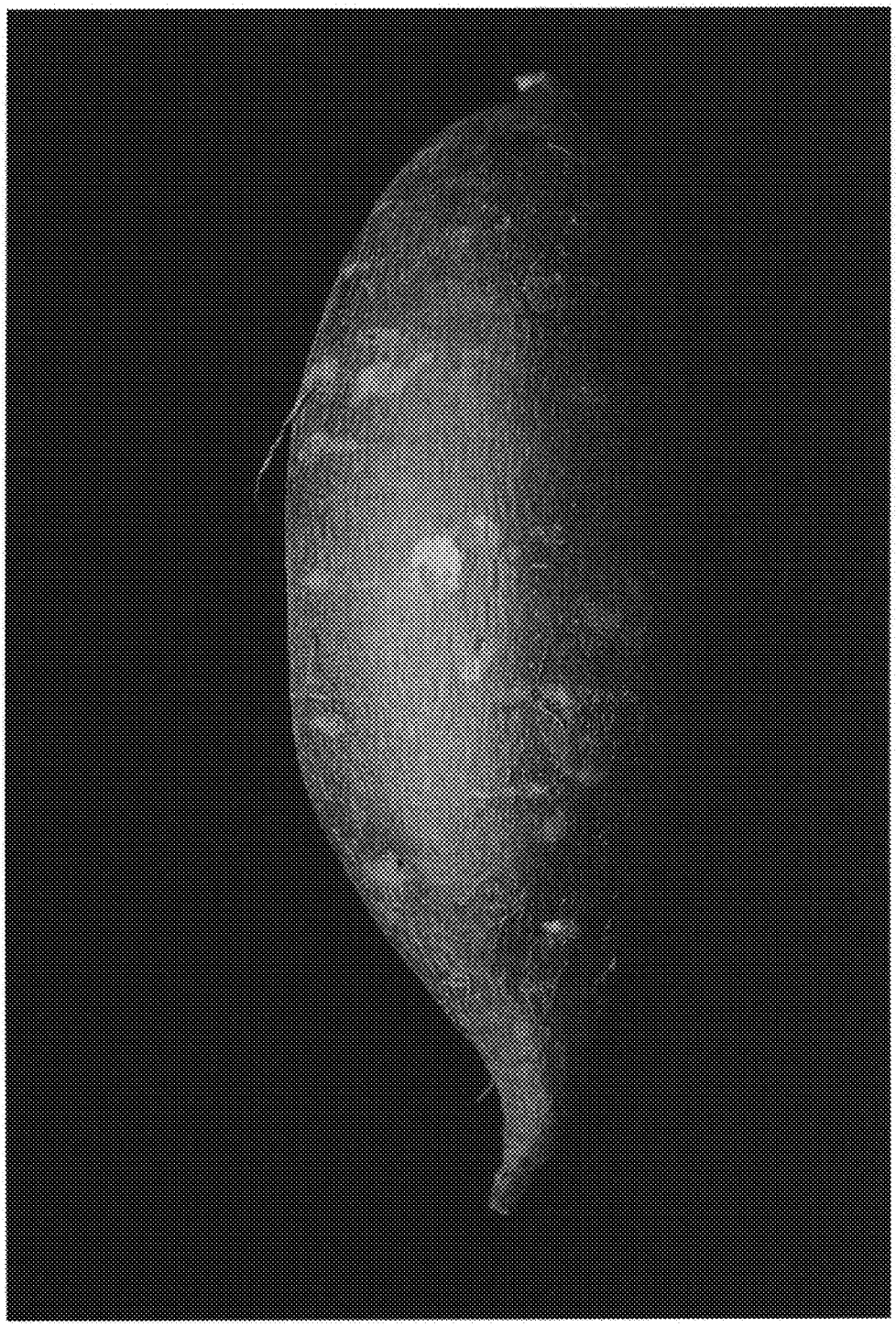
FIG. 1 is a color photograph of the fleshy root form of the novel variety of sweetpotato identified as 'LA13-81'.
Figure 2:
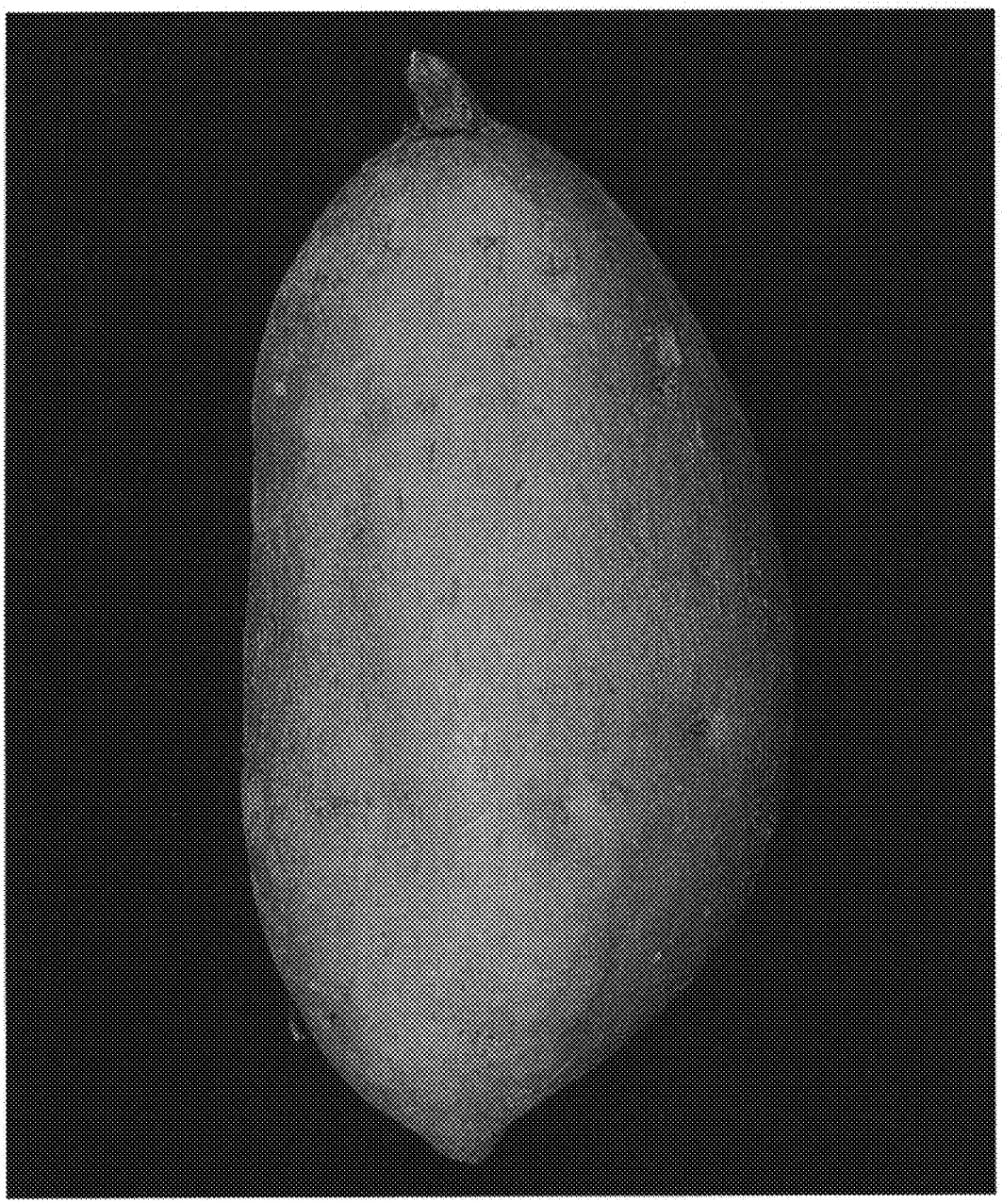
FIG. 2 is a color photograph of the fleshy root form of the sweetpotato variety identified as '05-111'.

FIG. 1 depicts the fleshy root form of the 'LA13-81' sweetpotato. The skin is a deep red-purple and differs from the light to medium rose '05-111', both at harvest and after several months of storage as shown in Table 1. No eyes or longitudinal grooving is present. MUNSELL® Book of Color values for skin and flesh for both 'LA13-81' and '05-111' storage roots are shown in Table 1. The '05-111' sweetpotato is depicted in FIG. 2. The skin for both 'LA13-81' and '05-111' was smooth. The 'LA13-81' cortex was 3.3 mm in depth and the color similar throughout. The flesh of 'LA13-81' is similar in comparison to '05-111'.

TABLE 1

| Variable | Variety | Color |
|---|---|---|
| Skin | 'LA13-81' | 7.5 R (red) P (purple) 3/8 |
| | '05-111' | 2.5 Y (yellow) R (red) 6/6 |
| Flesh | 'LA13-81' | 5 Y (yellow) R (red) 7/14 |
| | '05-111' | 2.5 Y (yellow) R (red) 7/8 |

Figure 3:
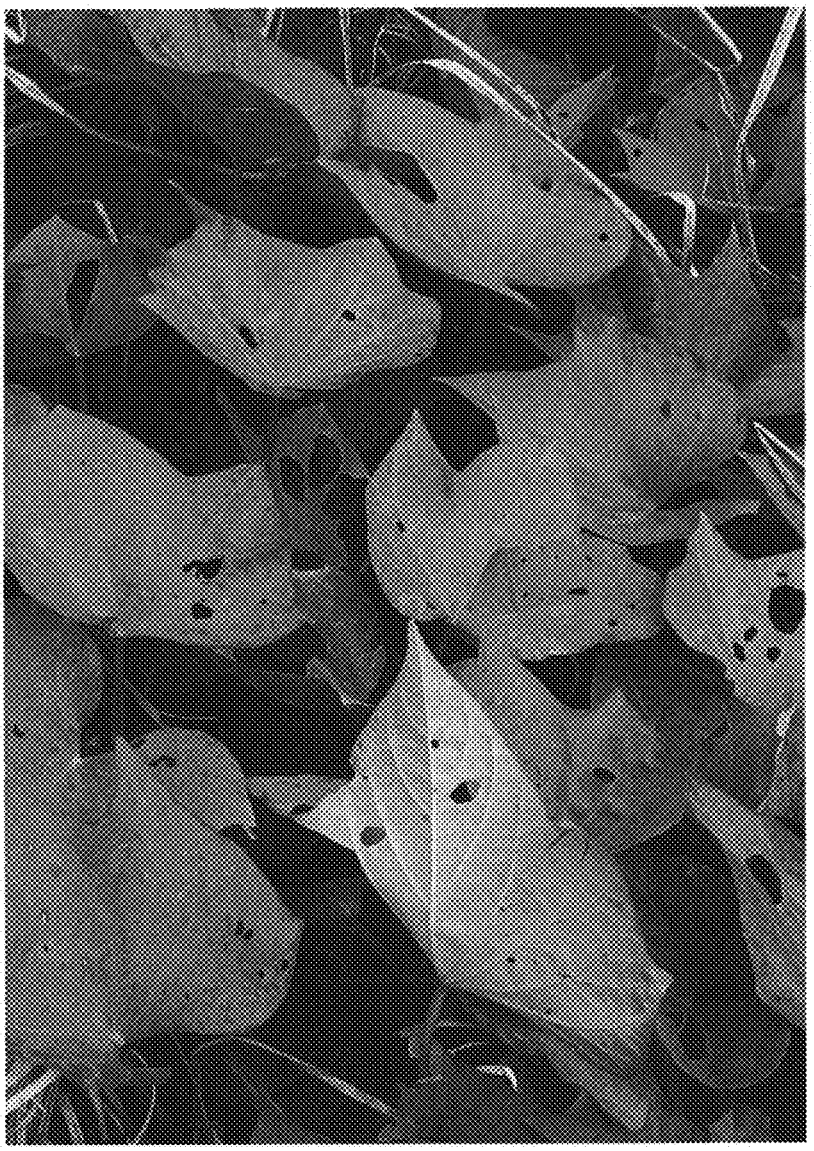
FIG. 3 is a color photograph of the canopy biomass of the novel variety of sweetpotato identified as 'LA13-81'.

FIG. 3 depicts the canopy biomass of 'LA13-81' sweetpotato. Stems of 'LA13-81' are green and remain unchanged [2.5 G (green) Y (yellow) (6/8)] except for an underlying red-purple hue [2.5 R (red) P (purple) (5/6)]. The 'LA13-81' canopy biomass appears similar to '05-111'. The 'LA13-81' canopy architecture was spreading and average (15-20) cm in height from the soil surface and comparable to '05-111'. For 'LA13-81', three to four main vines arose from the main stem near the soil surface. The stem giving rise to these vines was 2 cm in diameter; the 3-4 lateral vines were 294 cm in length with diameters of about 0.6 cm at 65 cm from the base and diameters of about 0.8 cm at the first internode of the first fully developed leaf from the apex. The spread is comparable to '05-111' and average. Seventeen lateral branches arose from each of the main vines. At the first internode from the apex, the internode length was about 4 cm between the first and second fully developed leaves. Internode lengths for other sections of the vine averaged about 4.1 cm. Unfolded immature leaves were green [2.5 G (green) Y (yellow) (4/6)] for the adaxial and abaxial surface, which change nominally over one to two nodes from the apex for the adaxial surface to a slightly lighter green lower surface [5 G (green) Y (yellow) (5/4)]. Anthocyanin pigmentation and pubescence were absent. Mature leaves at five nodes from the apex had an acute apex and mostly a cordate base and an entire leaf margin. Some leaves are shallow tricuspid. Mature leaves were about 9.2 cm long and 9.4 cm wide. Adaxial and abaxial veins were in a pinnate venation pattern and small in extent of purple [5 R (red) P (purple) (4/4)] pigmentation. Abaxial and adaxial surfaces were smooth. The petiole was green [2.5 G (green) Y (yellow) (5/6)]. A red-purple [5 R (red) P (purple) (2/6)] marking was at the base of the leaf junction with the petiole. The petiole was 8.2 cm long at five nodes from the apex, and 3.3 mm in diameter at 5 cm from the leaf junction. The dormant nodal meristem has slight red-purple marking [5 R (red) P (purple) (4/10)] which appears redder than the base of the leaf junction A typical inflorescence of 'LA13-81' displayed one cluster of three-five flowers per peduncle. Peduncles were green [10 G (green) Y (yellow) (5/8)], about 9 cm long, and about 3 mm in diameter. Individual flowers were about 3 cm long from the base of the calyx, and the corolla was 3 cm wide at the opening. The fused flower petals formed a pentagonal pattern with smooth edges. The inner throat of the corolla was purple [7.5 R (red) P (purple) (4/6)]. The inner and outer limbs of the corolla (corollas outermost area, distal from the calyx) were light purple [10 P (purple) (7/4)]. The five sepals comprising the calyx were elliptic with a cordate apex and was green [2.5 G (green) Y (yellow) (5/6)]; three of these sepals were about 12 mm long and 4.7 mm wide. Two other sepals (interspersed) were about 10 mm long and 3 mm wide. Sepal margins were entire. Stigmata were about 1.2 cm long and light purple [7.5R (red) P (purple) (8/4)] at the base before fading. Five stamens were inferior to the stigmata. A slight fragrance was present. Mature seed capsules are round and 6.3 mm in length and width, and seeds are 3.5 mm round. One black [neutral 1.75] seed is produced on average per capsule.

EXAMPLE 1

Tests Conducted

To confirm that 'LA13-81' was a new variety, controlled tests (e.g., pathogen responses and yield) were conducted in Baton Rouge, La. '05-111' was selected for comparison because of its importance in commercial United States orange flesh sweetpotato acreage. Diseases that commonly affect the growth of sweetpotatoes were selected to test for pathogen responses in both varieties. Scions of 'LA13-81' and '05-111' reacted similarly to most diseases evaluated in the controlled tests. 'LA13-81' was resistant and '05-111' was intermediate to resistant for *Streptomyces* soil rot caused by *Streptomyces ipomoeae* (Person & W. J. Martin) Waksman & Henrici. 'LA13-81' and '05-111' were resistant to *Fusarium* wilt or stem rot caused by *Fusarium oxysporum* Schlect. f sp. *batatas* (Wollenw.) Snyd. & Hans. 'LA13-81' was intermediate and '05-111' was resistant to *Rhizopus* soft rot caused by *Rhizopus stolonifer* (Ehr. ex. Fr.) Lind. 'LA13-81' was intermediate and '05-111' was susceptible to bacterial root rot caused by *Dickeya dadantii* Samson et al. as measured by postharvest inoculation of storage roots.

Nematode reproduction was measured in greenhouse tests. 'LA13-81' and '05-111' were very susceptible to race 3 of the southern root-knot nematode, *Meloidogyne incognita* (Kofoid & White 1919) Chitwood 1949.

'LA13-81' is drought and heat tolerant like '05-111' and succumbs to death at freezing like '05-111'.

'LA13-81' did not appear to show any novel insect resistance. 'LA13-81' has consistently ranked lower in banded cucumber beetle (*Diabrotica balteata* LeConte) in comparison to '05-111' in 2017 and 2018 trials.

To determine yield production, complete-block trials using three to four replications of 'LA13-81' and '05-111' each were conducted in 2016 and 2017 in areas of Louisiana, Mississippi, Arkansas, California and South Carolina likely to produce 'LA13-81'. 'LA13-81' and '05-111' sweetpotato plants were transplanted in randomized complete-block trials at 31 cm spacings. Each block/plot was fertilized with approximately 250 pounds per acre of a mixed fertilizer comprising 13% N, 13% $P_2O_5$, and 13% $K_2O$. 'LA13-81' was compared to '05-111' at transplanting dates in May-June. Average yields were measured for the following grades of roots: U.S. #1 (51-89 mm in diameter, 76-229 mm long); Canner (25-51 mm in diameter, 51-178 mm long); and Jumbo (larger than U.S. #1 in diameter, length or both, and without objectionable defects). A typical marketable root of 'LA13-81' was 180-190 mm long, 60-70 mm in diameter, with mostly elliptic shape. The base or distal end tended to be more elongated in comparison to slightly rounder apex (proximal end). U.S. #1 roots typically weighed 150-190 g.

A mid-season transplanting date trial was conducted at Senatobia, Miss. in 2017. 'LA13-81' and '05-111' were transplanted on May 24, 2017 and harvested on Sep. 19, 2017 (118 days after planting). Average yields, measured as Metric Tons per Hectare ($MT \cdot ha^{-1}$), for 'LA13-81' and '05-111' are shown in Table 2.

TABLE 2

Mid-season transplant date yield trial.

| Selection | US#1† | Canners† | Jumbos† | TMY‡† |
|---|---|---|---|---|
| 'LA13-81' | 58.49a | 21.24a | 0.00a | 79.45a |
| '05-111' | 32.26a | 16.87a | 4.15a | 52.22a |

†Average yields in $MT \cdot ha^{-1}$ of varieties followed by a common letter do not differ significantly ($P < 0.05$) according to Duncan's Multiple Range Test.
TMY‡ = total marketable yield A mid-season transplanting date trial was also conducted at Wynne, Ark. in 2017. 'LA13-81' and '05-111' were transplanted on Jun. 6, 2017 and harvested on Oct. 26, 2017 (121 days after planting). Average yields, measured as Metric Tons per Hectare ($MT \cdot ha^{-1}$), for 'LA13-81' and '05-111' are shown in Table 3.

TABLE 3

Mid-season transplant date yield trial.

| Selection | US#1† | Canners† | Jumbos† | TMY‡† |
|---|---|---|---|---|
| 'LA13-81' | 23.53a | 20.45a | 4.26a | 48.19a |
| '05-111' | 24.42a | 10.81a | 26.22b | 61.41b |

†Average yields in $MT \cdot ha^{-1}$ of varieties followed by a common letter do not differ significantly ($P < 0.05$) according to Duncan's Multiple Range Test.
TMY‡ = total marketable yield An early-season transplanting date trial was also conducted at Windsor, S.C. in 2017. 'LA13-81' and '05-111' were transplanted on May 18, 2017 and harvested on Nov. 11, 2017 (174 days after planting). Average yields, measured as Metric Tons per Hectare ($MT \cdot ha^{-1}$), for 'LA13-81' and '05-111' are shown in Table 4.

TABLE 4

Early-season transplant date yield trial.

| Selection | US#1† | Canners† | Jumbos† | TMY‡† |
|---|---|---|---|---|
| 'LA13-81' | 35.07a | 10.65a | 0a | 45.72a |
| '05-111' | 29.92a | 24.26a | 0a | 54.12a |

†Average yields in $MT \cdot ha^{-1}$ of varieties followed by a common letter do not differ significantly ($P < 0.05$) according to Duncan's Multiple Range Test.
TMY‡ = total marketable yield A mid-season transplanting date trial was also conducted at Forest, La. in 2016. 'LA13-81' and '05-111' were transplanted on May 31, 2016 and harvested on Oct. 29, 2016 (122 days after planting). Average yields, measured as Metric Tons per Hectare ($MT \cdot ha^{-1}$), for 'LA13-81' and '05-111' are shown in Table 5.

TABLE 5

Mid-season transplant date yield trial.

| Selection | US#1† | Canners† | Jumbos† | TMY‡† |
|---|---|---|---|---|
| 'LA13-81' | 22.13a | 10.98a | 1.29a | 34.4a |
| '05-111' | 22.36a | 13.78a | 7.68a | 43.82a |

†Average yields in $MT \cdot ha^{-1}$ of varieties followed by a common letter do not differ significantly ($P < 0.05$) according to Duncan's Multiple Range Test.
TMY‡ = total marketable yield An early-season transplanting date trial was also conducted at Livingston, Calif. in 2016. 'LA13-81' and '05-111' were transplanted on May 18, 2016 and harvested on Oct. 14, 2017 (149 days after planting). Average yields, measured as Metric Tons per Hectare ($MT \cdot ha^{-1}$), for 'LA13-81' and '05-111' are shown in Table 6.

TABLE 6

Early-season transplant date yield trial.

| Selection | US#1† | Canners† | Jumbos† | TMY‡† |
|---|---|---|---|---|
| 'LA13-81' | 26.63a | 9.77a | 15.77a | 52.16a |
| '05-111' | 29.09a | 7.80b | 10.95a | 47.84a |

†Average yields in $MT \cdot ha^{-1}$ of varieties followed by a common letter do not differ significantly ($P < 0.05$) according to Duncan's Multiple Range Test.
TMY‡ = total marketable yield As shown in Tables 2-6, 'LA13-81' produced yields comparable to '05-111' in regional trials at various planting dates. Yield in comparison to '05-111' in heavier silt loam soil (Table 5) were similar to outcomes in lighter, sandy loam soils (Tables 1, 2, 3, 4 and 6). Replicated plots at other farms and on station have shown 'LA13-81' has consistent yields for early, middle, or late season plantings. Yield declines are within norms in poor environments. 'LA13-81' had harvestable roots approximately 115-120 days after planting, which is typical development time for sweetpotatoes and comparable to '05-111'. The yield of Jumbo grade is indicative of earliness and 'LA13-81' was similar to the jumbo yield of '05-111'. In total, this data reflects consistent high yield characteristics for 'LA13-81'. 'LA13-81' has a storage life and shipping quality comparable to '05-111'.

'LA13-81' should be a valuable commercial sweetpotato variety. 'LA13-81' equals yield for US #1 and total marketable yield in comparison to '05-111' and represents a novel skin color useful in marketing as a specialty type red in premium retail environments.

We claim:

1. A new and distinct variety of *Ipomoea batatas* plant named 'LA13-81' as described and illustrated in the specification herein.

* * * * *